US006730800B2

(12) United States Patent
Fischer et al.

(10) Patent No.: US 6,730,800 B2
(45) Date of Patent: May 4, 2004

(54) METHOD FOR THE PRODUCTION OF TETRAHYDROFURAN

(75) Inventors: Rolf-Hartmuth Fischer, Heidelberg (DE); Frank Stein, Bad Dürkheim (DE); Rolf Pinkos, Bad Dürkheim (DE); Michael Hesse, Worms (DE); Michael Jolyon Sprague, Mannheim (DE); Markus Rösch, Oppenheim (DE); Holger Borchert, Offstein (DE); Stephan Schlitter, Limburgerhof (DE); Ralf-Thomas Rahn, Mannheim (DE); Alexander Weck, Freinsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/433,425

(22) PCT Filed: Dec. 7, 2001

(86) PCT No.: PCT/EP01/14394

§ 371 (c)(1),
(2), (4) Date: Jun. 4, 2003

(87) PCT Pub. No.: WO02/48128

PCT Pub. Date: Jun. 20, 2002

(65) Prior Publication Data

US 2004/0039214 A1 Feb. 26, 2004

(30) Foreign Application Priority Data

Dec. 11, 2000 (DE) .......................... 100 61 556

(51) Int. Cl.$^7$ .............................................. C07D 331/02
(52) U.S. Cl. ........................ 549/507; 549/429; 549/508
(58) Field of Search ................................ 549/429, 507, 549/508

(56) References Cited

FOREIGN PATENT DOCUMENTS

| EP | 322140 | * | 6/1989 |
|----|--------|---|--------|
| EP | 589314 | * | 3/1994 |

* cited by examiner

*Primary Examiner*—Amelia A. Owens
(74) *Attorney, Agent, or Firm*—Keil & Weinkauf

(57) ABSTRACT

Unsubstituted or alkyl-substituted THF is obtained by catalytic hydrogenation in the gas phase of $C_4$-dicarboxylic acids and/or their derivatives using a catalyst comprising <80% by weight, preferably <70% by weight, in particular from 10 to 65% by weight, of CuO and >20% by weight, preferably >30% by weight, in particular from 35 to 90% by weight, of an oxidic support having acid centers, at a hot spot temperature of from 240 to 310° C., preferably from 240 to 280° C., and a WHSV over the catalyst of from 0.01 to 1.0, preferably from 0.02 to 1, in particular from 0.05 to 0.5, kg of starting material/l of catalyst x hour.

20 Claims, No Drawings

METHOD FOR THE PRODUCTION OF TETRAHYDROFURAN

The present invention relates to a process for preparing unsubstituted or alkyl-substituted tetrahydrofuran by catalytic hydrogenation in the gas phase of substrates selected from the group consisting of derivatives of maleic acid and succinic acid and these acids themselves. For the purposes of the present invention, derivatives are anhydrides which, like the acids, may bear one or more alkyl substituents.

The preparation of tetrahydrofuran (THF) by gas-phase hydrogenation of maleic anhydride (MA) is a reaction which has been known for many years. Numerous catalyst systems for carrying out this catalytic reaction are described in the literature. Depending on the composition of the catalyst and the reaction parameters chosen, different product distributions are obtained using such catalysts.

It has been able to be shown that the hydrogenation of MA to THF forms firstly succinic anhydride (SA) and subsequently γ-butyrolactone (GBL) as intermediates and the latter can be hydrogenated further to form 1,4-butanediol (BDO). All the abovementioned intermediates can themselves be used as starting materials for preparing THF.

If GBL and THF bearing alkyl substituents are to be prepared, the alkyl-substituted species corresponding to the abovementioned starting materials can be used.

The catalysts used in the hydrogenation frequently comprise chromium, particularly in older processes. This is reflected in the patent literature in which there are a large number of patents and patent applications which disclose chromium-containing catalysts for the above-described hydrogenation reaction, with the hydrogenation in most cases being restricted to MA as starting material. U.S. Pat. No. 3,065,243 discloses a process in which copper chromite is employed as catalyst. According to the description and examples, this reaction results in formation of considerable amounts of SA which has to be circulated. As is known, process engineering problems due to crystallization of SA or succinic acid formed therefrom with subsequent blocking of pipes frequently occur.

Further copper chromite catalysts for the hydrogenation of MA are disclosed, for example, in U.S. Pat. Nos. 3,580,930, 4,006,165, EP-A 638 565 and WO 99/38856.

The catalysts used in U.S. Pat. No. 5,072,009 have the formula $Cu_tZn_bAl_cM_dO_x$ in which M is at least one element selected from the group consisting of the elements of groups IIA and IIIA, VA, VIII, Ag, Au, the elements of groups IIIB to VIIB and the lanthanides and actinides of the Periodic Table of the Elements, b is from 0.001 to 500, c is from 0.001 to 500 and d is from 0 to <200 and x corresponds to the number of oxygen atoms necessary according to valence criteria. In the examples, where only chromium-containing catalysts are used, the hydrogenation of MA using the catalysts of that invention forms THF in yields of over 90%.

EP-A 0 404 408 discloses a catalyst whose catalytically active material corresponds essentially to the material disclosed in the above-cited U.S. Pat. No. 5,072,009 for hydrogenation of MA. The catalytically active material is used in immobilized form on a support as coated catalyst and not as all-active catalyst. In contrast to the material present as all-active catalyst, mainly GBL is formed according to the examples reported, in which once again only chromium-containing catalysts are used.

A two-stage catalyst system for the hydrogenation of MA is described in U.S. Pat. No. 5,149,836. The catalyst for the first stage is chromium-free while the catalyst for the second stage is based on Cu—Zn—Cr oxides.

Owing to the toxicity of chromium, more modern technologies are increasing moving away from the use of chromium-containing catalysts. Examples of chromium-free catalyst systems may be found in WO 99/35139 (Cu—Zn oxide), WO 95/22539 (Cu—Zn—Zr) and U.S. Pat. No. 5,122,495 (Cu—Zn—Al oxide).

A catalyst made up exclusively of copper oxide and aluminum oxide for the gas-phase hydrogenation of MA to form GBL is disclosed in WO 97/24346. This catalyst comprises from 50 to 95% by weight, preferably from 80 to 90% by weight, of copper oxide, from 3 to 30% by weight, preferably from 5 to 15% by weight, of aluminum oxide and optionally a binder. Selectivities to GBL of up to about 98% are achieved in the hydrogenation of MA using such a catalyst.

WO 91/16132 discloses a chromium-free catalyst for the hydrogenation of MA. The catalyst comprises from 30 to 65% by weight of CuO, from 18 to 50% by weight of ZnO and from 8 to 22% by weight of $Al_2O_3$. Before use in the hydrogenation reaction, the catalyst is reduced in a hydrogen atmosphere and subsequently activated in a hydrogen atmosphere at not less than 400° C. for at least 8 hours. Such a catalyst gives GBL selectivities of about 90%.

In Catalysis Today 27 (1996), pp. 181 to 186, Castiglioni et al. disclose $CuO/ZnO/Al_2O_3$ catalysts which give mainly GBL in the hydrogenation of MA; a maximum THF selectivity of 17% is observed.

The use of a catalyst having a similar composition as in WO 97/24346 is also disclosed in JP 2 233 631. The object of that invention is to carry out the hydrogenation of MA in such a way that THF and BDO are formed as main products and only small amounts, if any, of GBL, are formed. This is achieved by use of catalysts based on mixed Cu—Al oxides and by adherence to particular reaction conditions. General indications of amounts of the Cu—Al oxide are not given; the examples disclose two catalyst compositions, one comprising about 46% by weight of CuO and 33% by weight of $Al_2O_3$ and the other comprising about 36% by weight of CuO and 47.% by weight of $Al_2O_3$. Use of this catalyst is said to give a THF selectivity of up to 99%, but only when an excess of GBL is employed as solvent. If the hydrogenation is carried out using the same catalyst in the absence of GBL, the selectivity drops to 76%. According to the examples, the hydrogenation is carried out at from about 210 to 230° C. and GHSVs of from about 3200 to 9600. The hydrogen/MA ratios are at values which are rather unfavorably high for industrial processes, namely from 200 to 800 in the examples.

The hydrogenation of MA under conditions corresponding to those of JP 2 233 631 but using a different catalyst is disclosed in JP 2 639 463. The use of the catalyst is said to make it possible to prepare BDO and THF by hydrogenation of MA. Use is made here of a copper oxide/zinc oxide/aluminum oxide catalyst whose composition is not disclosed quantitatively in the description. The catalysts used according to the examples have a composition of 20% by weight of CuO, 43.6% by weight of ZnO and 18.1% by weight of $Al_2O_3$, 32.6% by weight of CuO, 38.1% by weight of ZnO and 9.5% by weight of $Al_2O_3$, 24.2% by weight of CuO, 36.4% by weight of ZnO and 17.2% by weight of $Al_2O_3$, 26.4% by weight of CuO, 52.9% by weight of ZnO, 7.6% by weight of $Al_2O_3$ and 1.4% by weight of CaO or 22.9% by weight of CuO, 44.8% by weight of ZnO and 16.3% by weight of $Al_2O_3$. The hydrogenation is generally carried out using a solvent such as GBL or dioxane, giving a maximum THF selectivity of 94%. When the reaction is carried out without a solvent, the THF selectivity is no more than 83%.

The technologies on which the above-cited publications are based use prepurified MA which has, after its preparation, generally been freed of impurities by distillation as starting material for the hydrogenation reactions. MA is prepared by partial oxidation of particular hydrocarbons, namely benzene, butene mixtures and n-butane, with preference being given to using the latter. The crude product of the oxidation comprises not only the desired MA but also, in particular, by-products such as water, carbon monoxide, carbon dioxide, unreacted starting hydrocarbons and acetic and acrylic acids, with these by-products being independent of the hydrocarbons used in the oxidation. The by-products are usually separated off by complicated methods, for example by distillation as mentioned above. The purification is necessary because, in particular, the catalysts used in the hydrogenation process are generally sensitive to such impurities. Deactivation of the catalysts is a problem even when using purified MA, since coating of the catalyst with polymerization products of MA makes it necessary to regenerate the catalyst at generally relatively short intervals, often about 100 hours. The tendency for deactivation to occur is increased further when polymerizable impurities such as acrylic acid are present. This fact is known to those skilled in the art and is also described, for example, in the patent applications EP-A 322 140, WO 91/16132 and DE-A 240 44 93.

Up to now, the prior art contains only one publication which discloses the hydrogenation of MA which has been only roughly prepurified. WO 97/43234 discloses the absorption of maleic anhydride from gas streams which comprise maleic anhydride and originate from the oxidation of hydrocarbons by means of absorption media which have a boiling point at least 30° C. higher, stripping the maleic anhydride from these absorption media by means of hydrogen and hydrogenating the hydrogen stream comprising maleic anhydride in the gas phase over a heterogeneous catalyst. This gives mainly BDO together with small amounts of GBL and THF. The hydrogenation is carried out in the gas phase at from about 150° C. to 300° C. and a pressure of from 5 bar to 100 bar. Catalysts used are promoted copper catalysts as are described in Journal of Catalysis 150, pages 177 to 185 (1994). These are chromium-containing catalysts of the Cu/Mn/Ba/Cr and Cu/Zn/Mg/Cr types. Thus, according to the disclosure of that application, chromium-containing catalysts are used for the hydrogenation of MA grades containing the above-described impurities. However, owing to the toxicity of chromium, the use of chromium-containing catalysts is nowadays avoided as much as possible. In addition, the process forms not only the main product BDO but also appreciable amounts of undesired products, namely THF and GBL which either have to be separated off and purified or have to be returned to the hydrogenation. This is frequently associated with undesirable costs, particularly in industrial processes.

Which of the products GBL, THF and BDO obtainable in the hydrogenation of MA is the desired product often depends on the market growth of these products or their downstream products or on the wider product range of the respective producer. It can therefore be said that some producers use the hydrogenation of MA to produce THF while others use it for obtaining GBL and/or BDO.

It is an object of the present invention to provide a process by means of which THF can be prepared by hydrogenation of MA. This process should be able to be operated continuously using chromium-free catalysts and should give the largest possible amount of the desired product THF so as to achieve the best possible economics. Furthermore, the catalyst should be able to be employed with MA which has not been laboriously prepurified, for example by distillation, and nevertheless have a high stability, i.e. not require frequent regeneration.

We have found that this object is achieved by a process for preparing unsubstituted or alkyl-substituted THF by catalytic hydrogenation in the gas phase of $C_4$dicarboxylic acids and/or their derivatives using a catalyst comprising <80% by weight, preferably <70% by weight, in particular from 10 to 65% by weight, of CuO and >20% by weight, preferably >30% by weight, in particular from 35 to 90% by weight, of an oxidic support having acid centers, at a hot spot temperature of from 240 to 310° C., preferably from 240 to 280° C., and a WHSV over the catalyst of from 0.01 to 1.0, preferably from 0.02 to 1, in particular from 0.05 to 0.5, kg of starting material/l of catalyst x hour.

For the purposes of the present invention, the term $C_4$-dicarboxylic acids and their derivatives refers to maleic acid and succinic acid which may be unsubstituted or bear one or more $C_1$–$C_6$ alkyl substituents and also the anhydrides of these unsubstituted or alkyl-substituted acids. An example of such an acid is citraconic acid. Preference is given to using the anhydride of a given acid. Particular preference is given to using MA as starting material.

The process of the present invention can be operated inexpensively and gives high THF yields and selectivities. This is achieved by adherence to particular conditions and parameters. It is also possible to carry out the process continuously, which is preferred according to the present invention.

An important aspect is the choice of the catalyst, which comprises copper oxide as main catalytically active constituent. This is applied to an oxidic support which has to have a suitable number of acid centers. The amount of oxidic support required depends on the number of acid centers present therein. A suitable support material having a sufficient number of acid centers is aluminum oxide, whose use is preferred according to an embodiment of the present invention. According to another embodiment of the present invention, preference is given to using a combination of aluminum oxide with zinc oxide in a weight ratio of from 20:1 to 1:20, preferably from 5:1 to 1:5, as acid support material. In the case of materials having a large number of such acid centers, the lower limit of the amount of support consisting of such a material is 20% by weight. The amount of copper oxide is <80% by weight. Preferred catalyst compositions comprise <70% by weight of copper oxide and >30% by weight of support; particularly preferred catalysts comprise from 10 to 65% by weight of copper oxide and from 35 to 90% by weight of support.

Low copper oxide contents are preferred because of the cost advantage achieved in this way. High yields can be achieved as a result of the acid support materials.

The catalysts used according to the present invention, which are Cr-free, may optionally further comprise one or more additional metals or compounds thereof, preferably oxides, from groups 1 to 14 (IA to VIIIA and IB to IVB according to the old IUPAC nomenclature) of the Periodic Table of the Elements. If such a further oxide is used, preference is given to using $TiO_2$, $ZrO_2$, $SiO_2$ and/or MgO.

In addition, the catalysts used may contain from 0 to 10% by weight of an auxiliary. For the purposes of the present invention, auxiliaries are organic and inorganic materials which contribute to improved processability during catalyst production and/or to an increase in the mechanical strength of the shaped catalyst bodies. Such auxiliaries are known to those skilled in the art; examples include graphite, stearic acid, silica gel and copper powder.

The catalysts can be produced by methods known to those skilled in the art. Preference is given to methods in which the copper oxide is obtained in finely divided form and intimately mixed with the other constituents; particular preference is given to precipitation reactions. In such methods, precursor compounds dissolved in a solvent are precipitated by means of a precipitant in the presence of further soluble metal compounds or metal compounds suspended in the solvent, filtered, washed, dried and optionally calcined.

These starting materials can be processed by known methods to form the shaped bodies, for example by extrusion, tableting or by agglomeration processes, with or without addition of auxiliaries.

As an alternative, catalysts for use according to the present invention can also be produced, for example, by application of the active component to a support, for example by impregnation or vapor deposition. Furthermore, catalysts to be used according to the present invention can be obtained by shaping a heterogeneous mixture of active component or precursor compound thereof with a support component or precursor compound thereof.

In the hydrogenation according to the present invention, in which not only MA but also other, above-defined $C_4$-dicarboxylic acids or derivatives thereof can be used as starting material, the catalyst is employed in reduced, activated form. Activation is carried out by means of reducing gases, preferably hydrogen or hydrogen/inert gas mixtures, either before or after installation in the reactor in which the process of the present invention is carried out. If the catalyst has been installed in the reactor in oxidic form, activation can be carried out either before the plant is started up to carry out the hydrogenation according to the present invention or during the process, i.e. in situ. Separate activation before starting up the plant is generally carried out using reducing gases, preferably hydrogen or hydrogen/inert gas mixtures, at elevated temperatures, preferably from 100 to 300° C. In the in situ activation, activation is carried out by contact with hydrogen at elevated temperature while running up the plant.

The catalysts are used as shaped bodies. Examples include extrudates, ribbed. extrudates, other extruded shapes, pellets, rings, spheres and crushed material. The BET surface area of the copper catalysts in the oxidic state is from 10 to 400 $m^2/g$, preferably from 15 to 200 $m^2/g$, in particular from 20 to 150 $m^2/g$. The copper surface area ($N_2O$ decomposition) of the reduced catalyst in the installed state is >0.2 $m^2/g$, preferably >1 $m^2/g$, in particular >2 $m^2/g$.

In one variant of the invention, catalysts having a defined porosity are used. These catalysts display, as shaped bodies, a pore volume of $\geq 0.01$ ml/g for pore diameters of >50 nm, preferably $\geq 0.025$ ml/g for pore diameters of >100 nm and in particular $\geq 0.05$ ml/g for pore diameters of >200 nm. Furthermore, the ratio of macropores having a diameter of >50 nm to the total pore volume for pores having a diameter of >4 nm is >10%, preferably >20%, in particular >30%. The use of these catalysts often makes it possible to achieve high THF yields and selectivities. The porosities reported were determined by mercury intrusion in accordance with DIN 66133. The data were evaluated in the pore diameter range from 4 nm to 300 µm.

The catalysts used according to the present invention generally have a sufficient operating life. However, should the activity and/or selectivity of the catalyst drop during operation, it can be restored by means of measures known to those skilled in the art. These include, preferably, reductive treatment of the catalyst in a stream of hydrogen at elevated temperature. The reductive treatment may, if appropriate, be preceded by an oxidative treatment. Here, a gas mixture comprising molecular oxygen, for example air, is passed at elevated temperature through the catalyst bed. It is also possible to wash the catalyst with a suitable solvent, for example ethanol, THF or GBL, and subsequently to dry it in a stream of gas.

Furthermore, adherence to particular reaction parameters is necessary to achieve the THF selectivities according to the present invention.

An important parameter is adherence to a suitable reaction temperature. This is achieved, firstly, by means of a sufficiently high inlet temperature of the starting materials. This is from >220 to 300° C., preferably from 235 to 270° C. To obtain an acceptable or high THF selectivity and yield, the reaction has to be carried out so that a suitably high reaction temperature prevails in the catalyst bed in which the actual reaction takes place. This temperature, known as the hot spot temperature, is established after entry of the starting materials into the reactor and is in the range from 240 to 310° C., preferably from 240 to 280° C. The process is carried out so that the inlet temperature and the outlet temperature of the reaction gases are below this hot spot temperature. The hot spot is advantageously located in the first half of the reactor, particularly in the case of a shell-and-tube reactor. The hot spot temperature is preferably from 5 to 15° C., in particular from 10 to 15° C., above the inlet temperature. If the hydrogenation is carried out below the minimum temperatures for the inlet and hot spot temperatures respectively, the amount of GBL increases and the amount of THF decreases at the same time when using MA as starting material. Furthermore, deactivation of the catalyst due to coating with succinic acid, funaric acid and/or SA during the course of the hydrogenation is observed at such temperatures. On the other hand, if MA as starting material is hydrogenated at above the maximum temperatures for the inlet and hot spot temperatures respectively, the THF yield and selectivity drop to unsatisfactory values. In this case, increased formation of n-butanol and n-butane is observed, i.e. the products of a further hydrogenation.

The WHSV over the catalyst in the hydrogenation of the present invention is in the range from 0.01 to 1.0 kg of starting material/l of catalyst x hour. In the case of a possible but not preferred recirculation of intermediate formed by incomplete hydrogenation, GBL when using MA as starting material, the WHSV over the catalyst is the sum of fresh starting material fed in and recirculated intermediate. If the WHSV over the catalyst is increased beyond the specified range, an increase in the proportion of intermediate in the output from the hydrogenation is generally observed. The WHSV over the catalyst is preferably in the range from 0.02 to 1, in particular from 0.05 to 0.5, kg of starting material/l of catalyst x hour. In the case of recirculation, the term "starting material" also includes initially formed hydrogenation product which is then further hydrogenated after recirculation to form a product, i.e., for example, GBL when MA is used in the hydrogenation reaction.

The hydrogen/starting material molar ratio is likewise a parameter which has an important influence on the product distribution and the economics of the process of the present invention. From an economic point of view, a low hydrogen/starting material ratio is desirable. The lower limit is 5, but higher hydrogen/starting material molar ratios of from 20 to 400 are generally employed. The use of the above-described catalysts used according to the present invention and adherence to the above-described temperatures allows the use of favorable, low hydrogen/starting material ratios which are preferably in the range from 20 to 200, more preferably from 40 to 150. The most favorable range is from 50 to 100.

To set the hydrogen/starting material molar ratios used according to the present invention, part, advantageously the major part, of the hydrogen is circulated. For this purpose, circulating gas compressors known to those skilled in the art are generally used. The amount of hydrogen consumed chemically by the hydrogenation is replaced. In a preferred embodiment, part of the circulating gas is bled off to remove inerts, for example n-butane. The circulated hydrogen can also be used, if necessary after preheating, for vaporizing the starting material stream.

The volume flow of the reaction gases, generally expressed as GHSV (Gas Hourly Space Velocity) is also an important parameter in the process of the present invention. The GHSV in the process of the present invention is in the range from 100 to 10,000 Standard $m^3/m^3h$, preferably from 1000 to 3000 Standard $m^3/m^3h$, in particular from 1100 to 2500 Standard $m^3/m^3h$.

The pressure at which the hydrogenation of the present invention is carried out is in the range from 1 to 30 bar, preferably from 2 to 9 bar, in particular from 3 to 7 bar.

All products which are not condensed or only incompletely condensed on cooling the gas stream leaving the hydrogenation reactor are circulated together with the circulating hydrogen. These are predominantly THF, water and by-products such as methane and butane. The cooling temperature is from 0 to 60° C., preferably from 20 to 45° C. The THF content of the circulating gas is from 0.1 to 5% by volume, in particular from 1 to 3% by volume.

It is known from the literature that THF and GBL can be hydrogenated by means of hydrogen in the presence of copper catalysts to form n-butanol. The process of the present invention is notable for the fact that, despite the high proportions of THF in the circulating gas, which can generally be readily hydrogenated further to n-butanol, THF yields of over 90%, sometimes even over 95%, are achieved.

Possible types of reactor are all apparatuses suitable for heterogeneously catalyzed reactions involving a gaseous starting material and a product stream. Preference is given to tube reactors, shaft reactors or reactors with internal heat removal, for example shell-and-tube reactors; it is also possible to use a fluidized bed. Particular preference is given to using shell-and-tube reactors. It is possible to use a plurality of reactors connected in parallel or in series. In principle, streams can be fed in between the catalyst beds. Intermediate cooling between or in the catalyst beds is also possible. When using fixed-bed reactors, dilution of the catalyst by inert material is possible.

The gas stream leaving the reactor is cooled to from 10 to 60° C. The reaction products are condensed out in this way and are passed to a separator. The uncondensed gas stream is taken off from the separator and passed to the circulating gas compressor. A small amount of circulating gas is bled off. The condensed reaction products are taken continuously from the system and passed to work-up. By-products present in the condensed liquid phase are mainly n-butanol together with small amounts of propanol.

The hydrogenation product is then fractionally distilled to separate the azeotrope of water and unsubstituted or alkyl-substituted THF from any by-product, for example GBL. The water-containing THF is dewatered in a known manner and worked up by distillation to give THF which meets specifications. By-product such as GBL is returned to the hydrogenation or worked up by distillation.

In the process of the present invention, starting materials of differing purities can be used in the hydrogenation reaction. Of course, it is possible to use a high-purity starting material, in particular MA, in the hydrogenation reaction. However, the catalyst used according to the present invention and the other reaction conditions selected according to the present invention make it possible to use starting materials, in particular MA, which is/are contaminated by the customary compounds formed in the oxidation of benzene, butenes or n-butane and by any further components. The hydrogenation process of the present invention can thus, in a further embodiment, include an upstream step comprising the preparation of the starting material to be hydrogenated by partial oxidation of a suitable hydrocarbon and the separation of the starting material to be hydrogenated from the product stream obtained in this way.

In particular, this starting material to be hydrogenated is MA. Preference is given to using MA which originates from the partial oxidation of hydrocarbons. Suitable hydrocarbon streams are benzene, $C_4$-olefins (e.g. n-butenes, $C_4$ raffinate streams) or n-butane. Particular preference is given to using n-butane since it represents an inexpensive, economical starting material. Processes for the partial oxidation of n-butane are described, for example, in Ullmann'sEncyclopedia of Industrial Chemistry, 6th Edition, Electronic Release, Maleic and Fumarics Acids—Maleic Anhydride.

The reaction product obtained in this way is then taken up in a suitable organic solvent or solvent mixture which has a boiling point at atmospheric pressure which is at least 30° C. above that of MA.

This solvent (absorption medium) is brought to a temperature in the range from 20 to 160° C., preferably from 30 to 80° C. The gas stream comprising maleic anhydride from the partial oxidation can be brought into contact with the solvent in many ways: (i) passing the gas stream into the solvent (e.g. via gas introduction nozzles or sparging rings), (ii) spraying the solvent into the gas stream and (iii) countercurrent contact between the upflowing gas stream and the downflowing solvent in a tray column or packed column. In all three variants, the gas absorption apparatuses known to those skilled in the art can be used. When choosing the solvent to be used, care has to be taken to ensure that it does not react with the starting material, for example the MA which is preferably used. Suitable solvents are tricresyl phosphate, dibutyl maleate, high molecular weight waxes, aromatic hydrocarbons having a molecular weight of from 150 to 400 and a boiling point above 140° C., for example dibenzylbenzene; dialkyl phthalates having $C_1$–$C_8$-alkyl groups, for example dimethyl phthalate, diethyl phthalate, dibutyl phthalate, di-npropyl phthalate and diisopropyl phthalate; mono-, di-, tri- und tetraesters of cyclohexanedi-, tri- und tetraacids, the esters being alkyl-, cycloalkyl-, hydroxyund alkoxyalkylesters having 1 to 30, preferably 2 to 20, in particular 3 to 18 carbon atoms and—in the case of non-cyclic groups—being linear or branched; non-limiting examples comprise: dialkyl cyclohexane-1,4-dicarboxylates with identical alcohol groups, dialkyl cyclohexane1,3-dicarboxylates with identical alcohol groups, dialkyl cyclohexane-1,2-dicarboxylates with identical alcohol groups, mixed esters of cyclohexane-1,2-dicarboxylic acid with C1 to C13-alcohols, mixed esters of cyclohexane-1,3-dicarboxylic acid with C1 to C13-alcohols, mixed esters of cyclohexane-1,4-dicarboxylic acid with C1 to C13-alcohols, alkyl esters of cyclohexane-1,2,4-tricarboxylic acid, alkyl esters of cyclohexane-1,3,5-tricarboxylic acid, alkyl esters of cyclohexane-1,2,3-tricarboxylic acid, alkyl esters of cyclohexane-1,2,4,5-tetracarboxylic acid; mono-, di-, tri- und tetraesters of cyclohexenedi-, tri- und tetraacids, the esters being alkyl-, cycloalkyl-, hydroxy- und alkoxyalkylesters having 1 to 30, preferably 2 to 20, in particular 3 to 18 carbon atoms and—in the case of non-cyclic groups—being linear or branched; non-limiting examples comprise: dialkyl cyclohexene-1,4-dicarboxylates with identical alcohol groups, dialkyl cyclohexene-1,3-dicarboxylates with identical alcohol groups, dialkyl cyclohexene-1,2-dicarboxylates with identical alcohol groups, mixed esters of cyclohexene-1,2-dicarboxylic acid with C1 to C13-alcohols, mixed esters of cyclohexene-1,3-dicarboxylic acid with C1 to C13-alcohols, mixed esters of cyclohexene-1,4-dicarboxylic acid with C1 to C13-alcohols, alkyl esters of cyclohexene-1,2,4-tricarboxylic acid, alkyl esters of cyclohexene-1,3,5-tricarboxylic acid, alkyl esters of cyclohexene-1,2,3-tricarboxylic acid, alkyl esters of cyclohexene-1,2,4,5-tetracarboxylic acid; di-$C_1$–$C_4$-alkyl esters of other aromatic and aliphatic dicarboxylic acids, for example dimethyl naphthalene-2,3-dicarboxylate, methyl esters of long-chain fatty acids having, for example, from 14 to 30 carbon atoms, high-boiling ethers, for example dimethyl ethers of polyethylene glycols, for example tetraethylene glycol dimethyl ether.

The use of phthalates is preferred.

The solution resulting from treatment with the absorption medium generally has an MA content of from about 5 to 400 grams per liter.

The waste gas stream remaining after treatment with the absorption medium comprises mainly the by-products of the preceding partial oxidation, e.g. water, carbon monoxide, carbon dioxide, unreacted butanes, acetic acid and acrylic acid. The waste gas stream is virtually free of MA.

The dissolved MA is subsequently stripped from the absorption medium. This is carried out using hydrogen at or at most 10% above the pressure of the subsequent hydrogenation or alternatively under reduced pressure with subsequent condensation of remaining MA. In the stripping column, a temperature profile determined by the boiling points of MA at the top of the column and the virtually MA-free absorption medium at the bottom at the prevailing column pressure and the chosen dilution with carrier gas (in the first case with hydrogen) is observed. In the case of direct stripping with hydrogen, a temperature at the top of 130° C. and a pressure of 5 bar are employed.

To prevent losses of solvent, rectification internals can be located above the feed point for the crude MA stream. The virtually MA-free absorption medium taken off at the bottom is returned to the absorption zone. In the case of direct stripping with hydrogen, a stream of gas virtually saturated with MA is taken off at the top of the column at 180° C. and a pressure of 5 bar. The $H_2$/MA ratio is from about 20 to 400. Otherwise, the condensed MA is pumped to a vaporizer and vaporized there into the circulating gas stream.

The MA/hydrogen stream further comprises by-products formed in the partial oxidation of n-butane, butenes or benzene by means of oxygen-containing gases and also absorption medium which has not been separated off. These additional components are primarily acetic acid and acrylic acid as by-products, water, maleic acid and the dialkyl phthalates which are preferably used as absorption media. The MA contains from 0.01 to 1% by weight, preferably from 0.1 to 0.8% by weight, of acetic acid and from 0.01 to 1% by weight, preferably from 0.1 to 0.8% by weight, of acrylic acid, based on MA. In the hydrogenation step, acetic acid and acrylic acid are completely or partly hydrogenated to form ethanol or propanol. The maleic acid content is from 0.01 to 1% by weight, in particular from 0.05 to 0.3% by weight, based on MA.

If dialkyl phthalates are used as absorption media, the amounts of them present in the MA depend strongly on correct operation of the stripping column, in particular the enrichment section. Phthalate contents of 1.0% by weight, in particular 0.5% by weight, should not be exceeded under suitable operating conditions, since otherwise the consumption of absorption media becomes too high.

The hydrogen/maleic anhydride stream obtained in this way is then passed to the hydrogenation zone and hydrogenated as described above. Compared to the use of substantially prepurified, for example by distillation, MA, the catalyst activity and operating life is virtually unchanged. The process of the present invention makes it possible to obtain THF yields of about 90%, in favorable cases about 95%. A high product selectivity is achieved at the same time. GBL is usually formed in amounts of less than 5%.

The process of the present invention is illustrated by the examples below.

EXAMPLES

Example 1 a) Catalyst Production 1.5 l of water are placed in a heatable precipitation vessel provided with a stirrer and are heated to 80° C. Over a period of one hour, a metal salt solution comprising 731 g of $Cu(NO_3)_2 * 2.5\ H_2O$ and 1840 g of $Al(NO_3)_3 * 9\ H_2O$ in 2000 ml of water and at the same time a 20% strength by weight sodium carbonate solution are metered into this precipitation vessel while stirring until a pH of 8 is reached in the precipitation vessel. The mixture is stirred at this pH for another 15 minutes. The total consumption of sodium carbonate solution is 5.6 kg. The suspension formed is filtered and the solid is washed with water until the washings no longer contain nitrate (<25 ppm). The filter cake is firstly dried at 120° C. and subsequently calcined at 600° C. The catalyst produced in this way comprises 50% by weight of CuO and 50% by weight of $Al_2O_3$. 400 g of this catalyst powder are comminuted to a particle size of <1 mm, admixed with 12 g of graphite powder, intimately mixed and pressed to form pellets having a diameter of 3 mm and a height of 3 mm.

b) Catalyst Activation

Before the commencement of the reaction, the catalyst is subjected to a treatment with hydrogen in the hydrogenation apparatus. For this purpose, the reactor is heated to 180° C. and the catalyst is activated at atmospheric pressure for the time indicated in Table 1 using the mixture of hydrogen and nitrogen specified in each case.

TABLE 1

| Time (minutes) | Hydrogen (Standard l/h) | Nitrogen (Standard l/h) |
|---|---|---|
| 120 | 10 | 550 |
| 30 | 25 | 400 |
| 15 | 60 | 100 |
| 180 | 60 | 0 | c) Hydrogenation Apparatus

The pressure apparatus used for the hydrogenation comprises a vaporizer, a reactor, a condenser with feed line for quench, a feed line for hydrogen, a waste gas line and a circulating gas blower. The pressure in the apparatus is kept constant.

The molten MA is pumped from the top into the preheated (245° C.) vaporizer and vaporized. A mixture of fresh hydrogen and circulating gas is likewise introduced into the vaporizer from the top. Hydrogen and MA thus flow from the bottom to the heated reactor. The contents of the reactor comprise a mixture of glass rings and catalyst. After the hydrogenation, the THF formed together with water, other reaction products and hydrogen leaves the reactor and is condensed in the condenser by quenching. Part of the circulating gas is bled off before the remainder, mixed with fresh hydrogen, flows back into the vaporizer.

The condensed liquid reaction mixture, the waste gas and the circulating gas are analyzed quantitatively by gas chromatography.

Example 1d d) Hydrogenation of Maleic Anhydride Prepared from n-butane

The reactor of the hydrogenation apparatus described in Example 1b is charged with 220 ml of the catalyst produced in Example 1a and 130 ml of glass rings. Activation was carried out as described in Example 1b.

The starting material used is maleic anhydride prepared from n-butane and containing 500 ppm of acrylic acid, 1500 ppm of acetic acid and 100 ppm of dibutyl phthalate. The reaction is carried out for 1000 hours. During the whole of this time, no deactivation of the catalyst, i.e. no decrease in the maleic anhydride conversion and/or the tetrahydrofuran yield, is observed. Butanediol is not detected by gas chromatography. Table 2 summarizes the reaction parameters for the hydrogenation and the results.

After fractional distillation of the hydrogenation products, tetrahydrofuran is isolated in a purity of 99.96%. This THF meets the specification for use as starting material for poly THF.

Example 1e

In place of the catalyst comprising 50% by weight of CuO and 50% by weight of $Al_2O_3$, a catalyst having the composition 40% by weight of CuO, 40% by weight of ZnO and 20% by weight of $Al_2O_3$ is used. This too is, after activation, operated for 1000 hours using the maleic anhydride described in Example 1d without deactivation being observed. Butanediol is not detected by gas chromatography. Table 2 summarizes the reaction parameters for the hydrogenation and the results. After fractional distillation of the hydrogenation products, tetrahydrofuran is isolated in a purity of 99.94%.

TABLE 2

| Example | Temp. (° C.) | Pressure (bar) | GHSV ($h^{-1}$) | WHSV catalyst (kg/lh) | Molar ratio $H_2$:MA | Conversion[3] (%) | Mol % | | | |
|---|---|---|---|---|---|---|---|---|---|---|
| | | | | | | | THF | GBL | n-BuOH | n-Butane |
| 1d[1] | 255–258 | 5.1 | 2000 | 0.1 | 85:1 | 100 | 87–88 | 4–5 | 6 | 0.1 |
| 1e[2] | | | 2000 | 0.1 | | | 87 | 3 | 5 | 0.1 | n-BuOH = n-butanol
[1]Catalyst: 50% by weight CuO, 50% by weight $Al_2O_3$
[2]Catalyst: 40% by weight CuO, 40% by weight ZnO, 20% by weight $Al_2O_3$
[3]Total conversion of MA and succinic anhydride (SA)

The results of Examples 1d and 1e show that an unchanged high catalyst activity together with unchanged tetrahydrofuran yields are achieved over long reaction times in the continuous hydrogenation of maleic anhydride in which acrylic acid, acetic acid and dibutyl phthalate are present over $Cu/Al_2O_3$ and $Cu/ZnO/Al_2O_3$ catalysts. In addition, the hydrogenation products can be worked up by distillation to give tetrahydrofuran of high purity which meets the required tetrahydrofuran specification.

Example 2

A catalyst comprising 60% of copper oxide and 40% of aluminum oxide and produced in a manner analogous to Example 1a is installed in the above-described hydrogenation apparatus and pretreated with hydrogen as described in Example 1b. The starting material used is maleic anhydride prepared from n-butane and containing 5000 ppm of acrylic acid, 1500 ppm of acetic acid and 100 ppm of dibutyl phthalate. The reaction is carried out at a pressure of 5 bar; all other reaction parameters and results are shown in Table 3. Examples 2a, 2b and 2d are comparative experiments carried out under reaction conditions outside the parameters employed according to the present invention.

TABLE 3

| Example | Temp. (° C.) | Pressure (bar) | GHSV ($h^{-1}$) | WHSV catalyst (kg/lh) | Molar ratio $H_2$:MA | Mol % | | | |
|---|---|---|---|---|---|---|---|---|---|
| | | | | | | THF | GBL | n-BuOH | n-Butane |
| 2a[1] | 235 | 5 | 5000 | 0.04 | 550:1 | 86.0 | 2.0 | 9.0 | 1.0 |
| 2b[1] | | | 2700 | 0.12 | 100:1 | 58.6 | 36.7 | 2.3 | 0.3 |
| 2c | 255 | | 2700 | 0.13 | 90:1 | 89.4 | 2.6 | 7.0 | 1.0 |
| 2d[1] | 285 | | 2700 | 0.13 | 90:1 | 65.3 | — | 12.5 | 19.6 |

[1]Comparative examples

The result of Example 2c shows that high tetrahydrofuran yields are achieved at 255° C. If, as in Example 2b, the temperature is reduced to 235° C., the butyrolactone yield increases to 36.7%. Only by lowering the WHSV over the catalyst to a third and increasing the hydrogen/maleic anhydride ratio (Example 2a) is a tetrahydrofuran yield approaching that of Example 2c obtained. If (Example 2d) the hydrogenation temperature is increased to 285° C., the tetrahydrofuran yield drops to 65.3%.

Example 3

Example 2c is repeated at a GHSV of 1800 h$^{-1}$ under otherwise identical conditions using a catalyst comprising 60% of CuO and 40% of Al$_2$O$_3$. The tetrahydrofuran yield is 93%. Butyrolactone is not observed.

Example 4 (Comparative Example)

Example 3 of JP 2-233 631 is repeated: for this purpose, the Cu/Al$_2$O$_3$ catalyst described in Example 3 is produced by the method indicated there. The pure MA/GBL mixture is then hydrogenated under the conditions indicated. This gives a THF yield of 90% and a GBL yield of 7%, also 1.9% of n-butanol.

On changing from MA/GBL (molar ratio=1:3) to pure MA (molar amount of pure MA corresponds to the sum of the molar amounts of MA+GBL, WHSV over the catalyst= 0.03 kg of MA/l of catalyst x hour) as feed, the THF yield drops to 12% of THF and 59% of GBL after 10 hours. In addition, 28% of maleic acid and succinic acid (based on MA used) are formed (Table 4). Large amounts of dicarboxylic acid mixture were deposited in the outlet section of the hydrogenation apparatus and in the circulating gas system.

TABLE 4

| Example | MA conversion (%) | (Mol %)[2] | | | | |
|---------|---|---|---|---|---|---|
| | | THF | GBL | BDO[3] | n-BuOH | n-Butane |
| 4[1] | About 95 | 12 | 59 | — | 0.6 | — |

[1] Comparative example
[2] Based on MA used
[3] 1,4-Butanediol

The results show that only very low THF yields are achieved under the conditions of Example 3 of JP 2-233 631 when using MA in place of MA/GBL mixtures. Despite low WHSVs over the catalyst, blockages caused by solids (dicarboxylic acid mixtures) occur in the hydrogenation plant and these make it impossible to carry out the MA hydrogenation on an industrial scale.

We claim:

1. A process for preparing unsubstituted or alkyl-substituted THF by catalytic hydrogenation in the gas phase of C$_4$-dicarboxylic acids or their derivatives using a catalyst comprising <80% by weight of CuO and >20% by weight of an oxidic support having acid centers, at a hot spot temperature of from 240 to 310° C. and a WHSV over the catalyst of from 0.01 to 1.0 kg of starting material/l of catalyst x hour.

2. A process as claimed in claim 1, wherein the catalyst comprises 10 to 65% by weight of CuO an oxidic support.

3. A process as claimed in claim 1, wherein the catalyst comprises 35 to 90% by weight of CuO anoxidic support.

4. A process as claimed in claim 1, wherein the oxidic support is Al$_2$O$_3$ or a combination of Al$_2$O$_3$/ZnO in a weight ratio of from 20:1 to 1:20.

5. A process as claimed in claim 1, carried out at pressures of from 1 to 30 bar.

6. A process as claimed in claim 1, wherein the molar ratio of hydrogen/starting material is from 20 to 400.

7. A process as claimed in claim 1, wherein the GHSV is from 100 to 10,000 Standard m$^3$/m$^3$h.

8. A process as claimed in claim 1, wherein the inlet temperature is from >220 to 300° C. and is from about 5 to 15° C. below the hot spot temperature.

9. A process as claimed in claim 1, wherein the hot spot is located in the first half of the reactor.

10. A process as claimed in claim 1, wherein one or more further metals or compounds thereof, from the group consisting of the elements of groups 1 to 14 of the Periodic Table of the Elements are present in the catalyst.

11. A process as claimed in claim 10, wherein a substance selected from the group consisting of ZrO$_2$, TiO$_2$, SiO$_2$ and MgO is present in the catalyst.

12. A process as claimed in claim 1, wherein the catalyst is activated by reduction before or after installation in the reactor and before use in the hydrogeneration reaction.

13. A process as claimed in claim 1, wherein the catalyst further comprises an auxiliary in an amount of <10% by weight, selected from graphite, stearic acid, silica gel and copper powder.

14. A process as claimed in claim 1, wherein the shaped catalyst body has a pore volume of ≧0.01 ml/g for pore diameter of >50 nm.

15. A process as claimed in claim 1, wherein the ratio of macropores having a diameter of >50 nm to the total pore volume for pores having a diameter of >4 nm in the shaped catalyst body is >10%.

16. A process as claimed in claim 1, wherein a fixed-bed reactor, a shaft reactor, a fluidized-bed reactor or a reactor with internal heat removal is used.

17. A process as claimed in claim 1, wherein maleic anhydride is used as starting material for the reaction.

18. A process as claimed in claim 1, wherein maleic anhydride prepared by oxidation of benzene, C$_4$-olefins or n-butane, where the crude maleic anhydride obtained by oxidation has been extracted from the crude product mixture using a solvent and has subsequently been stripped from this solvent by means of hydrogen, is used.

19. A process as claimed in claim 1, wherein the absorption medium is selected from the group consisting of tricresyl phosphate, dibutyl maleate, high molecular weight waxes, aromatic hydrocarbons having a molecular weight in the range from 150 to 400 and a boiling point above 140° C., di-C$_1$–C$_4$-alkyl esters of aromatic and aliphatic dicarboxylic acids, methyl esters of long-chain fatty acids having from 14 to 30 carbon atoms, high-boiling ethers, dimethyl ethers of polyethylene glycols, and dialkyl phthalates having C$_1$–C$_8$-alkyl groups.

20. A process as claimed in claim 1, wherein the maleic anhydride is stripped from the absorption medium under reduced pressure or at pressures which correspond to the pressure in the hydrogenation or are at most 10% above this pressure.

* * * * *